US011234587B2

(12) United States Patent
Lees, Jr. et al.

(10) Patent No.: US 11,234,587 B2
(45) Date of Patent: Feb. 1, 2022

(54) MULTI-LAYERED SPECULUM AND METHODS OF MANUFACTURING AND USING SAME

(71) Applicants: James J. Lees, Jr., Medford, NJ (US); Tamatha Britt Fenster, Scarsdale, NY (US); Yaotsung Mitchell Tung, Basking Ridge, NJ (US)

(72) Inventors: James J. Lees, Jr., Medford, NJ (US); Tamatha Britt Fenster, Scarsdale, NY (US); Yaotsung Mitchell Tung, Basking Ridge, NJ (US)

(73) Assignee: ARTISAN MEDICAL DEVICES CORPORATION, Medford, NJ (US)

( * ) Notice: Subject to any disclaimer, the term of this patent is extended or adjusted under 35 U.S.C. 154(b) by 249 days.

(21) Appl. No.: 16/779,723

(22) Filed: Feb. 3, 2020

(65) Prior Publication Data
US 2020/0253467 A1    Aug. 13, 2020

Related U.S. Application Data

(60) Provisional application No. 62/802,262, filed on Feb. 7, 2019.

(51) Int. Cl.
*A61B 1/32* (2006.01)
*A61B 1/00* (2006.01)
*A61B 1/303* (2006.01)

(52) U.S. Cl.
CPC .............. *A61B 1/32* (2013.01); *A61B 1/0011* (2013.01); *A61B 1/00135* (2013.01); *A61B 1/303* (2013.01)

(58) Field of Classification Search
CPC ........... A61B 1/32; A61B 17/42; A61B 17/02; A61B 17/0218; A61M 2025/0024; A61M 29/00; A61F 2/92; A61F 2/93
See application file for complete search history.

(56) References Cited

U.S. PATENT DOCUMENTS

| 4,994,070 | A | 2/1991 | Waters |
| 5,010,895 | A | 4/1991 | Maurer et al. |
| 9,763,733 | B2 * | 9/2017 | Jameson ............ A61B 18/1492 |
| 2008/0058604 | A1 * | 3/2008 | Sorensen ................ A61B 1/32 600/208 |
| 2010/0317926 | A1 * | 12/2010 | Kaul ........................ A61B 1/32 600/210 |
| 2012/0158033 | A1 | 6/2012 | Deal et al. |
| 2018/0043133 | A1 * | 2/2018 | Wong ................ A61M 25/0108 |
| 2021/0177461 | A1 * | 6/2021 | Baril ...................... A61B 17/02 |

FOREIGN PATENT DOCUMENTS

| CN | 205549205 U | 9/2016 |
| CN | 106963333 A | 7/2017 |

OTHER PUBLICATIONS

Written Opinion of Searching Authority in PCT/US2020/016372, dated Jun. 4, 2020.

* cited by examiner

*Primary Examiner* — Wade Miles
(74) *Attorney, Agent, or Firm* — Wei & Sleman LLP

(57) ABSTRACT

A speculum includes an insulating sleeve having a body, the body having a first side edge, a second side edge, a front edge and a back edge, and a metallic sheet having a first end, a second end, a front end and a back end, the back end being tailored to match a back edge of the sleeve, the metallic sheet being covered by the body of the sleeve.

7 Claims, 6 Drawing Sheets

MULTI-LAYERED SPECULUM AND METHODS OF MANUFACTURING AND USING SAME

CROSS-REFERENCE TO RELATED APPLICATIONS

The present disclosure claims priority to U.S. provisional application, Ser. No. 62/802,262 filed Feb. 7, 2019, the contents of which are hereby incorporated by reference in its entirety as if fully set forth herein.

FIELD OF THE DISCLOSURE

The present disclosure relates to speculums for use in medical settings. More particularly the present disclosure relates to multi-layered speculums having features to increase patient comfort and ease of use.

BACKGROUND OF THE DISCLOSURE

Surgical instruments, such as a speculum, are used to examine body orifices or cavities. One example is a vaginal speculum of simple construction, typically made of two pieces molded from plastic. Such speculums are often used in procedures, such as Loop Electrosurgical Excision Procedures (LEEP).

Traditional speculums are difficult to handle and awkward to use when other instruments are needed (e.g., a suction device or a probe). Additionally, traditional speculums include screws and pry apart in an up/down fashion, making them uncomfortable for the patient.

SUMMARY OF THE DISCLOSURE

In some embodiments, a speculum includes an insulating sleeve having a body, the body having a first side edge, a second side edge, a front edge and a back edge, and a metallic sheet having first end, a second end, a front end and a back end, the back end being tailored to match a back edge of the sleeve, the metallic sheet being overmolded with the body of the sleeve.

In some embodiments, a method of forming a speculum includes providing a metallic sheet having a first end, a second end, a front end and a back end, the back end having a plurality of indentations and projections, and overmolding an insulating sleeve having a body on the metallic sheet, the body having a first side edge, a second side edge, a front edge and a back edge, the sleeve forming a plurality of independently moveable petals around the projections of the sheet.

BRIEF DESCRIPTION OF THE DISCLOSURE

Various embodiments of the presently disclosed speculums are described herein with reference to the drawings, wherein.

Figure 3A:
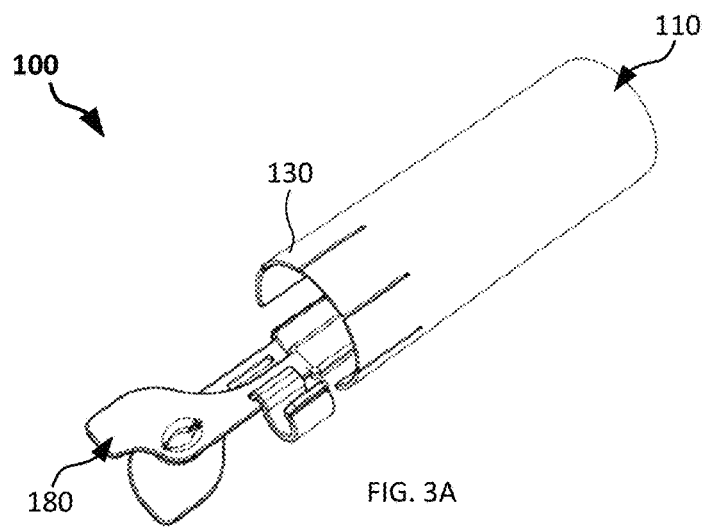
Figure 3B:
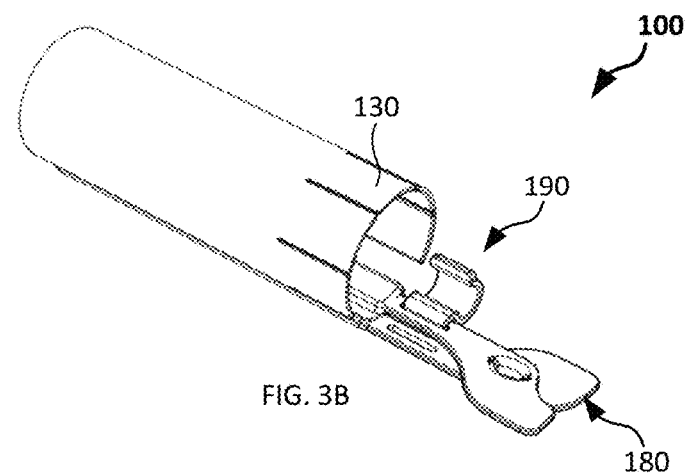
Figure 3C:
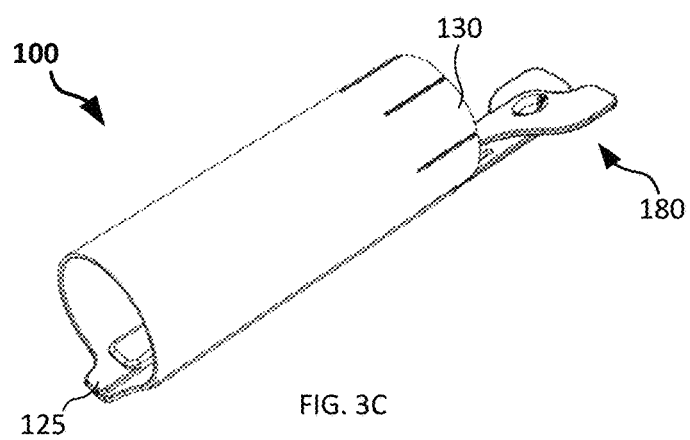
Figure 4A:
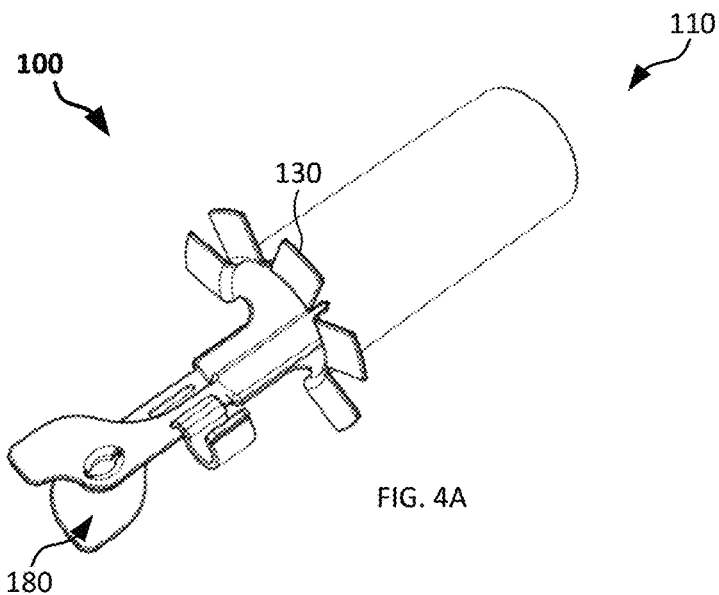
Figure 4B:
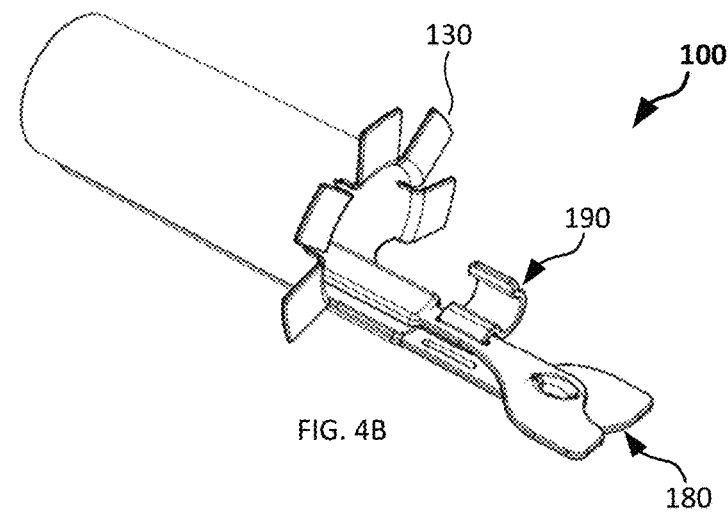
Figure 4C:
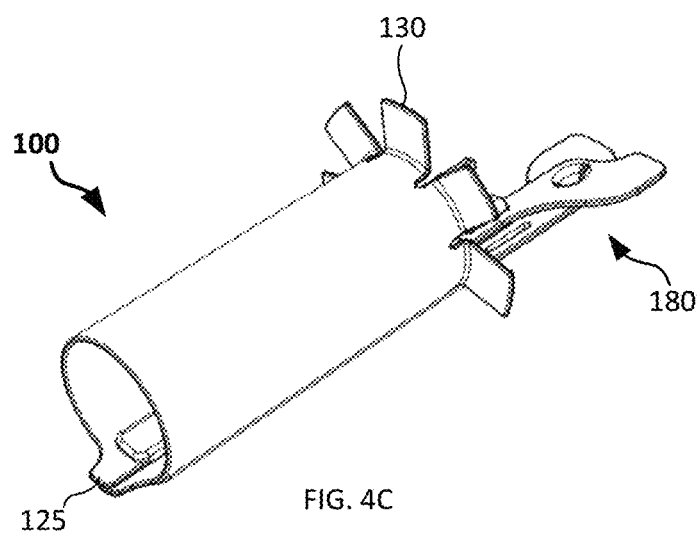
Figure 5:
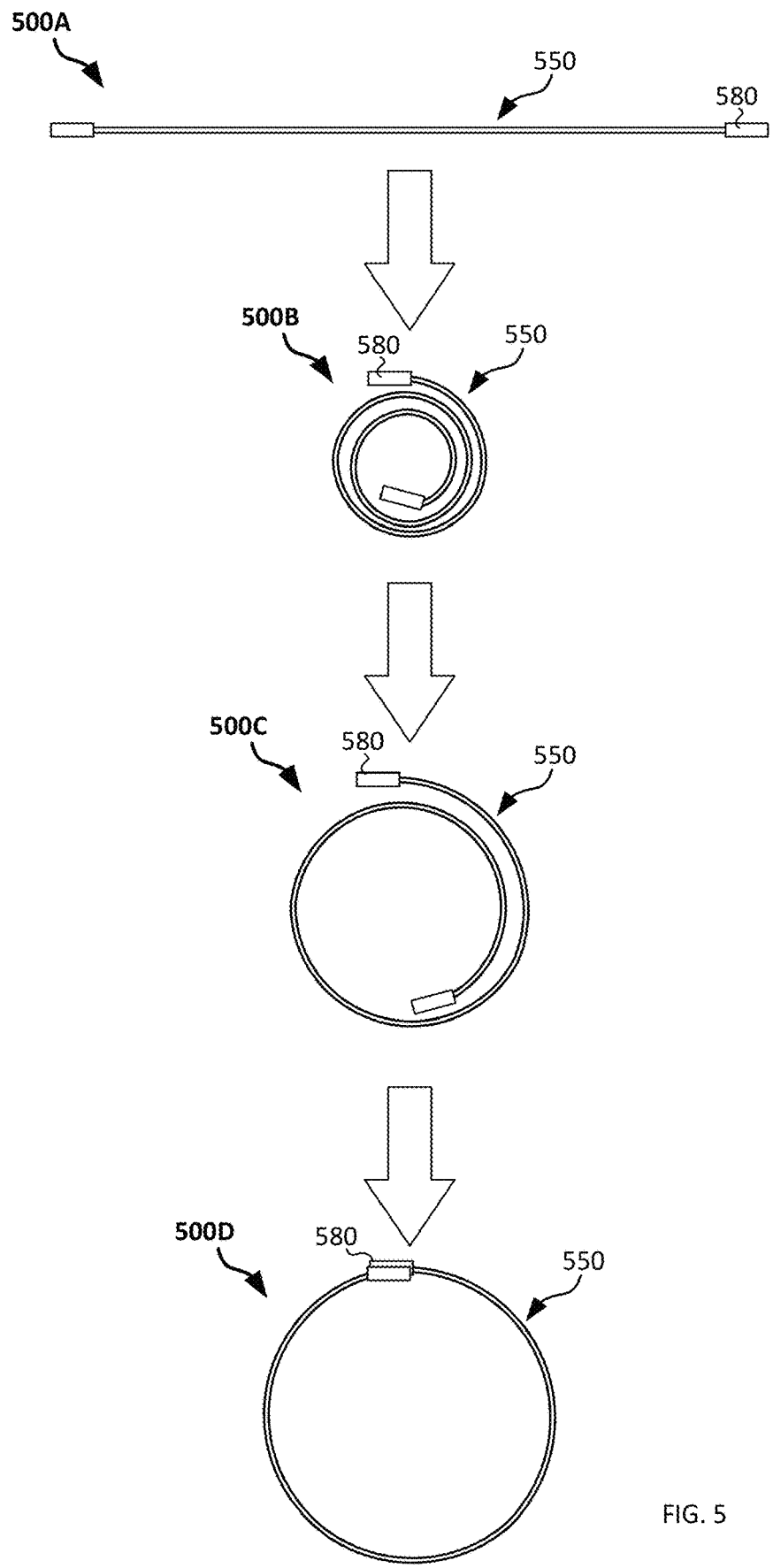
Figure 6A:
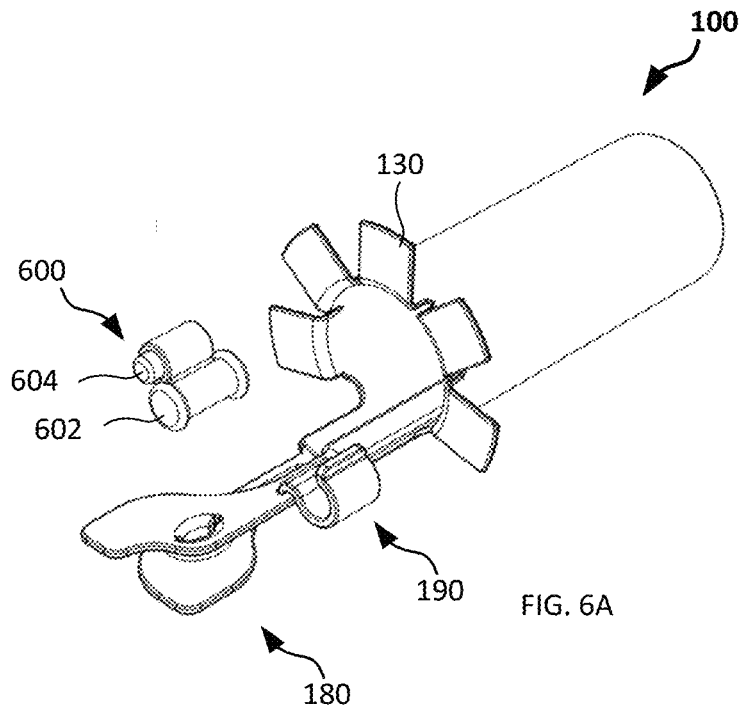
Figure 6B:
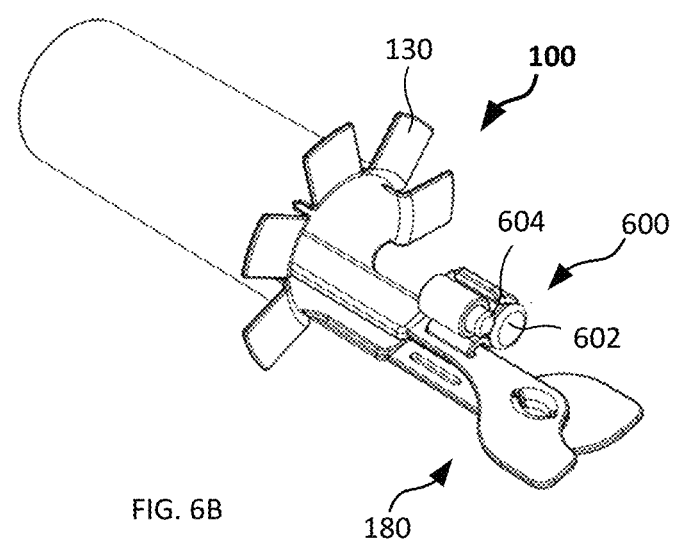

FIGS. 3A-C are schematic perspective views of an assembled speculum in a first condition;

FIGS. 4A-C are schematic perspective views of an assembled speculum in a second condition; and FIG. 5 is a schematic representation of top views of an assembled device in various configurations; and FIGS. 6A-B are schematic perspective views showing an assembled speculum with a light module detached and attached, respectively.

Various embodiments of the present invention will now be described with reference to the appended drawings. It is to be appreciated that these drawings depict only some embodiments of the invention and are therefore not to be considered limiting of its scope.

DETAILED DESCRIPTION

Despite the various improvements that have been made to speculums, conventional devices suffer from some shortcomings as described above.

There therefore is a need for further improvements to the devices, systems, and methods of manufacturing and using speculums. Among other advantages, the present disclosure may address one or more of these needs.

As used herein, the term "proximal," when used in connection with a component of a speculum, refers to the end of the component closest to the physician when the speculum is inserted in a patient, whereas the term "distal," when used in connection with a component of a speculum, refers to the end of the component farthest from the physician when the assembly is inserted in a patient.

Likewise, the terms "trailing" and "leading" are to be taken as relative to the operator (e.g., physician) of the speculum assembly. "Trailing" is to be understood as relatively close to the operator, and "leading" is to be understood as relatively farther away from the operator.

Figure 1:
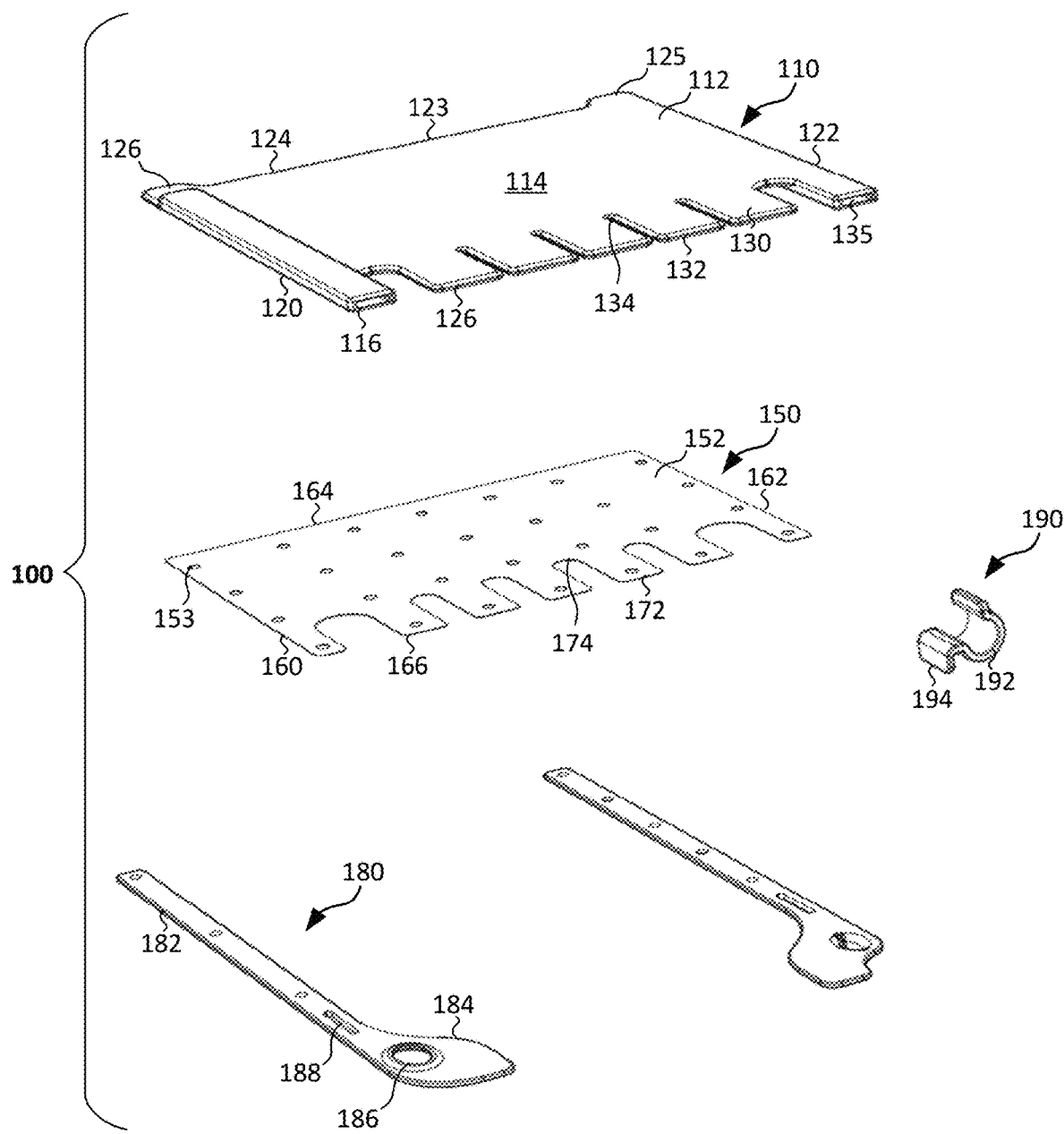
FIG. 1 is a schematic perspective view of unassembled components of a speculum.

FIG. 1 illustrates the components of a speculum 100 in the unassembled condition. Each component will be discussed independently, then the assembly of the components will be explained. As shown, speculum 100 generally includes a sleeve 110, a metallic sheet 150, a pair of arms 180 and a clip 190.

A soft, insulating sleeve 110 may be formed of a polymeric material, such as silicone or an elastomer, such as a thermoplastic elastomer, or other suitable non-conductive material and may include a generally rectangular body 112 defined between first side edge 120, second side edge 122, front (or proximal) edge 124 and back (or distal) edge 126. Sleeve 110 may serve to provide 360-degree protection to the patient's anatomy from cautery procedures as will be described in greater detail below. Body 122 may be formed of a material having upper layer 114, lower layer 116 and a spacing therebetween sized to receive the sheet. As will be described below, the sleeve may be also be formed by overmolding it over a sheet so that portions of the sleeve cover upper and lower surfaces of the sheet. Front edge 124 may include a tapered portion 123 disposed between the side edges, and a projecting tip 125 disposed adjacent at least one of the side edges. Back edge 126 may define a plurality of petals 130 defined by a series of projections 132 and indentations 134. Any number of petals 130 may be formed. As shown, the device includes five petals 130, although two, three, four, five, six, seven, eight or more petals may be formed. Additionally, sleeve 110 may include a pair of pockets 135, each disposed at one of the side edges for receiving a portion of the arms. In embodiments where the sleeve is overmolded, portions of the sleeve may also be overmolded onto a portion of the arms to couple the arms to the sleeve and the sheet.

Metallic sheet 150 may be disposed within sleeve 110. In at least some examples, sheet 150 may be formed of stainless steel, or any suitable material that is both thin and strong, while being flexible enough to be rolled to a spiral or cylindrical configuration having a small diameter. Alternatively, sheet 150 may be formed of a nonmetallic material, such as polycarbonate. Sheet 150 may be formed of a material having greater rigidity than sleeve 110. Sheet 150 may have body 152 defined by side ends 160,162, a front end 164 and a back end 166. Front end 164 and side ends 160,162 may be substantially straight. Conversely, back end 166 may have an oscillating pattern that is tapered to match that of petals 130 of sleeve 110 including complementary projections 172 and indentations 174. Sheet 150 may also include a plurality of holes 153 arranged in rows along the body to increase fixation and strengthening the bond between the sheet and the sleeve. In overmolded configurations, the material of the sleeve will be introduced into these holes of the sheet to increase fixation between the two components.

A pair of arms 180 are also provided, each arm having an elongated body 182 configured to fit within a pocket 135 of sleeve 110, and an enlarged handle 184. In some examples, each enlarged handle 184 includes an aperture 186, the two apertures having male or female features to make them capable of mating with one another to couple the two handles together. Thus, one handle will include an aperture with a male feature, and the second aperture will include a female feature, and the two will be coupled together to keep the device in the tubular configuration as will be described in greater detail below. Additionally, each arm may include a slit 188 configured to receive a portion of a clip to couple the clip to the handles.

Clip 190 may be substantially C-shaped and include a cavity 192 for housing a portion of an instrument, such as a probe, a suction device, or a light (not shown). Clip 190 may further include an affixing member 194 configured, sized and arranged to be disposed within one or more of slits 188 of arms 180.

Figure 2A:
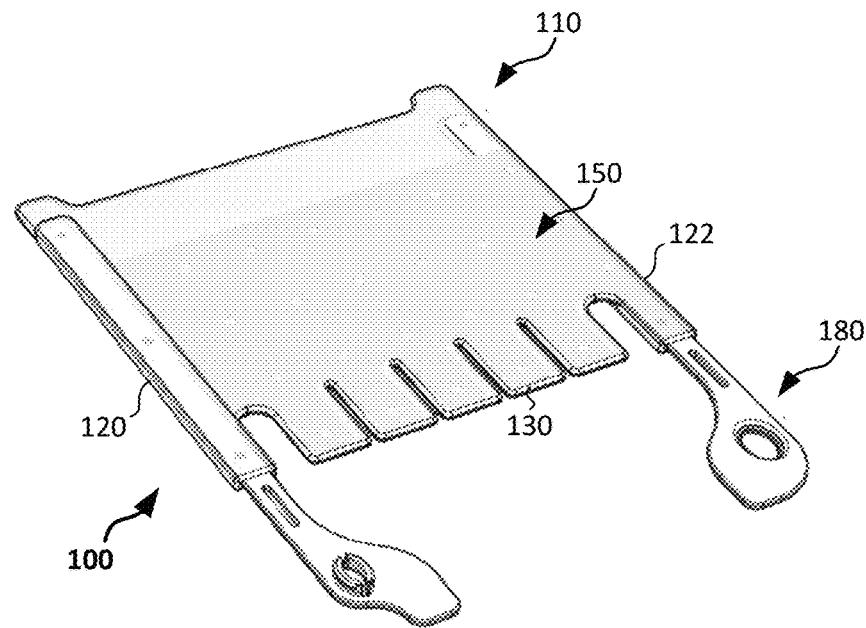
FIGS. 2A and 2B are schematic top and bottom perspective views of a partially assembled speculum.
Figure 2B:
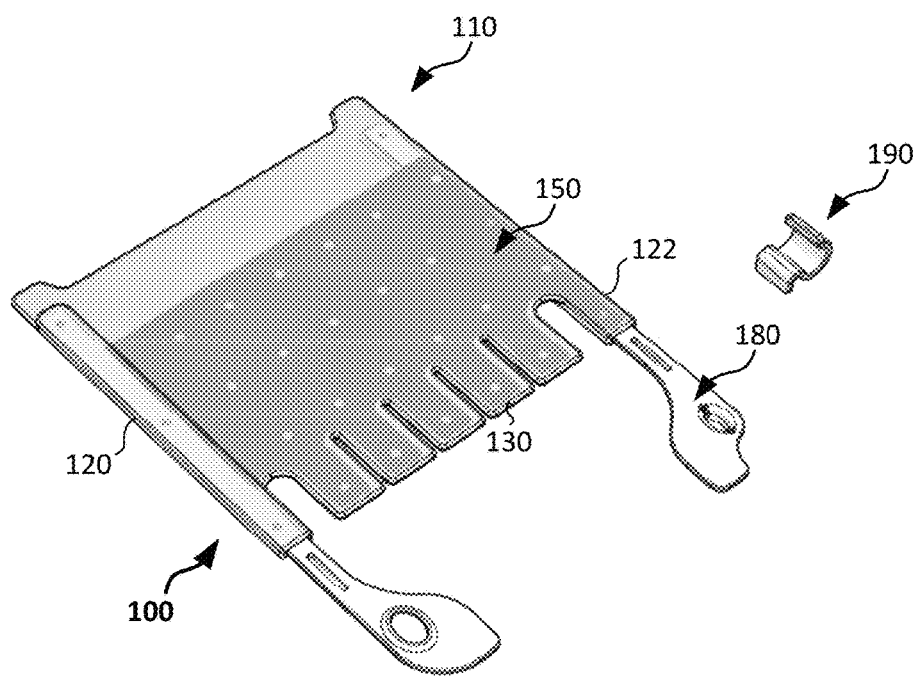

FIGS. 2A-B show the metallic sheet 150 being covered by the sleeve 110. It will be understood that instead of forming the sheet, the sleeve and the arms separately and assembling the device by placing the sheet inside the sleeve, that sleeve 110 may be simply overmolded onto sheet 150. For example, in one embodiment, the two handles may be injection molded, and the metallic sheet may be die-cut. The metallic sheet may then be attached to the two handles, and the handles with the sheet are then placed in a mold having a cavity in the shape of the sleeve. The sleeve, in one case a thermoplastic elastomer, may then be injected into the cavity to form around the handles and the metal sleeve, the sleeve material flowing through the holes of the sheet to increase bonding between the sleeve and the sheet. In some examples, the sleeve will completely envelop the sheet as well as portions of the arms. Thus, the sheet 150 and the arms 180 are disposed within the sleeve 100 and bonded therein so that they are affixed therein. A few features will be readily appreciated from FIGS. 2A-B. First, sheet 150 is entirely covered by sleeve 110, and a substantial portion of the sleeve 110 extends beyond the front end of the sheet 150. Additionally, each of the petals 130 of sleeve 110 includes a complementary petal-like portion of the metallic sheet as shown to increase its rigidity.

Generally, the speculum may transition between a number of configurations. To illustrate this, FIG. 5 is provided which shows a top view of a speculum having sleeve 550 and handles 580 transitioning from a flat first configuration 500A, to a tightly rolled spiral second configuration 500B, to a loosely rolled spiral third configuration 500C, and finally to a fourth cylindrical configuration 500D. In the flat configuration 500A, the devices are capable of being efficiently transported and stored. When being prepared for use, the amount of overlapping of the sleeve will determine the diameter of the device as shown in FIG. 5. For example, the device may start as a flat sheet, and may be rolled tightly into a tight spiral configuration 500B the size of a tampon, where the sleeve forms a spiral having three or more overlapping portions, making insertion less traumatic. The device may be gently unrolled to a slightly looser spiral 500C, and then eventually to a cylindrical configuration 500D. The features of the device will be examined in greater detail with respect to the cylindrical configuration.

FIGS. 3A-C show the device of FIGS. 1 and 2 being rolled from a flat configuration to form a generally tubular or cylindrical structure. In the rolled tubular configurations, side edges 120,122 are disposed next to, or partially overlapping, one another. As the device is unraveled, the arms 180 are also brought together and overlap one another and are affixed together at the apertures. Tips 125 of the sleeve also at least partially overlap one another to form a unitary tip for manipulating or lifting tissue (e.g., the anterior lip of the cervix). Note that in one embodiment, the tip is formed on a same side of the cylindrical sleeve as the handles.

As shown, clip 190 is also affixed to the slit 188 of one of the arms 180. The clip 190 is disposed in a position that is spaced away from the center of the tubular structure. That is, the tubular speculum forms a diameter having a center defining a central axis, and the clip is disposed off this central axis in an eccentric position, being closer to one wall of the sleeve than an opposing wall. With this configuration, clip 190 is capable of retaining a first instrument (e.g., a suction device, a light or probe), while leaving the center of the device unobstructed for introduction and/or manipulation of a second instrument. Moreover, the petals 130 of the speculum 100 are shown in a first, collapsed condition, where they are aligned with the walls of the tubular structure.

These petals 130 may be independently opened to a second, expanded condition as shown in FIG. 4A-C. In this expanded condition, the petals 130 are angled radially outward away from the tubular structure. In at least some examples, the petals may be capable of projecting to a second position that is orthogonal to the walls of the tubular structure or at any position between the first position and the second position. By opening any number or all of the petals to this second condition, visibility of the interior of the speculum (and the tissue) may be increased to accommodate differences in patient anatomy. For example, by adjusting the size/length, the range of motion of instrument used with the speculum may be increased. Thus, the petals may allow an instrument to make a sharp 120-degree ascent into the uterus. Additionally, opening of the petals serves to shorten the length of the tubular structure allowing for greater maneuverability of the device and the instruments to be disposed therein.

Turning to FIGS. 6A-B, a light module 600 is shown being used with a speculum 100, the speculum being fully assembled and disposed in the open cylindrical configuration. Speculum 100 includes clip 190 as previously described that is coupled to one of the handles, and a detachable light module 600 is provided. Light module 600 generally includes a pair of cylindrical components including a fixation member 602, and a light-generating member 604. Fixation member 602 may be shaped and sized to be coupled and decoupled to the speculum via a friction fit with clip 190. In one example, light-generating member 604 may include a battery-powered LED or other suitable lighting component. When fixation member 602 is attached to clip 190 (FIG. 6B), light-generating member 604 may be centrally disposed within the speculum 100 (e.g., the light-generating member 604 may be disposed along the central axis defined by the walls of the speculum).

In use, a speculum may be formed in any of the embodiments described above. The speculum may include a metallic sheet to provide rigidity, and an insulating material formed on the metallic sheet, the insulating material being compliant to provide comfort to the patient and providing protection to the patient from cautery procedures. Handles may be used to grasp and operate the device, and the tip of the device may be used to manipulate patient tissue. In some examples, a procedure may require the use of additional instrumentation. A clip may be optionally used to hold a portion of an instrument in an eccentric position, leaving the center of the speculum unobstructed for the introduction of additional instruments.

The speculum may be used in connection with a LEEP procedure. In such a procedure, the speculum is placed in the vagina and the cervix is isolated. Diseased cells are identified with specific solutions. Once highlighted, the cellular pathology is excised using a thin low voltage electrified wire loop that is inserted through the speculum. Two modes may be used, in cutting mode the high frequency current is produced in a smooth uninterrupted sine wave. As the loop is applied to the cervical tissue an arc occurs near the point of contact and the cells rapidly heat and explode into steam. The steam envelope allows for continued arcing, extending the cut with little coagulation artifact. In coagulation mode, tissue is fulgurated with short bursts of high peak voltage current. Typically, both modalities are combined in a blend mode. The procedure lends itself to ease of use in an office setting. Local anesthesia is typically administered, although in certain situations a more monitored operative setting with general anesthesia may be preferred.

A variety of wire loops are available to choose from in order to tailor the specimen to the anatomy of the patient and the characteristics of the lesion. For example, a loop may be chosen that allows excision of the transformation zone to an adequate depth without contact to the vaginal side wall. The loop may be attached to a pencil-like base that is controlled with a foot switch. Current may be applied as the loop contacts the cervix and the specimen is excised. An additional endocervical specimen may be excised as necessary. The excision bed is then commonly fulgurated to reduce bleeding.

By performing a LEEP procedure through the instant speculum, the speculum may be used for both dilation and for protecting the surrounding areas from the current. Specifically, insulating sleeve forms a substantially cylindrical structure, the walls of the cylindrical structure being non-conductive, and serving to protect the patient's tissue.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

What is claimed is:

1. A speculum comprising:

an insulating sleeve having a body, the body having a first side edge, a second side edge, a front edge, and a back edge; and a metallic sheet having a first end, a second end, a front end, a back end, an upper surface, and a lower surface, the back end being tailored to match a back edge of the sleeve, the metallic sheet being covered by the body of the sleeve on the upper surface and the lower surface, wherein the metallic sheet includes a plurality of holes formed therethrough, and the sleeve extends partially through at least one of the plurality of holes.

2. A speculum comprising:

an insulating sleeve having a body, the body having a first side edge, a second side edge, a front edge, and a back edge; and a metallic sheet having a first end, a second end, a front end, a back end, an upper surface and a lower surface, the back end being tailored to match a back edge of the sleeve, the metallic sheet being covered by the body of the sleeve on the upper surface and the lower surface, wherein the sleeve further includes pockets at the side edges.

3. The speculum of claim 2, further comprising a pair of arms disposed within the pockets, each of the pair of arms having an elongated body, and an enlarged handle.

4. The speculum of claim 3, wherein each of the pair of arms further includes an aperture defined in the enlarged handle and a slit defined in the elongated body.

5. The speculum of claim 4, further comprising a clip coupleable to at least one of the pair of arms, the clip having a C-shaped cavity for accepting an instrument.

6. The speculum of claim 5, wherein the clip is configured and arranged to hold the instrument in an eccentric position.

7. A speculum comprising:

and insulating sleeve having a body, the body having first side edge, a second side edge, a front edge and a back edge; and a metallic sheet having a first end, a second end, a front end, a back end, an upper surface and a lower surface, the back end being tailored to match a back edge of the sleeve, the upper surface and the lower surface, wherein the sleeve is rolled to form a tubular structure such that the first side edge and the second side edge of the sleeve, are disposed adjacent one another, wherein the back edge includes a plurality of petals defined by a series or projections and indentations and, wherein each one of the plurality of petals is capable of being independently transitionable between a first condition aligned with the tubular structure and a second condition that is angled radially outward away from the tubular structure.

* * * * *